United States Patent
Kenyon et al.

(10) Patent No.: US 10,363,385 B2
(45) Date of Patent: Jul. 30, 2019

(54) RESPIRATORY APPARATUS

(71) Applicant: ResMed Limited, Bella Vista, New South Wales (AU)

(72) Inventors: Barton John Kenyon, Sydney (AU); Renee Frances Flower, Sydney (AU); Enrico Brambilla, Irvine, CA (US); Philip Rodney Kwok, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 368 days.

(21) Appl. No.: 15/194,663

(22) Filed: Jun. 28, 2016

(65) Prior Publication Data

US 2016/0303338 A1    Oct. 20, 2016

Related U.S. Application Data

(63) Continuation of application No. 14/177,354, filed on Feb. 11, 2014, now Pat. No. 9,381,318, which is a (Continued)

(51) Int. Cl.
*A61M 16/06* (2006.01)
*A61M 16/00* (2006.01)
(Continued)

(52) U.S. Cl.
CPC .... *A61M 16/0066* (2013.01); *A61M 16/0057* (2013.01); *A61M 16/021* (2017.08);
(Continued)

(58) Field of Classification Search
CPC .............. A61M 16/00; A61M 16/0057; A61M 16/0066; A61M 16/0069; A61M 16/105;
(Continued)

(56) References Cited

U.S. PATENT DOCUMENTS 3,822,698 A * 7/1974 Guy ..................... A62B 18/045
                                                      128/201.25
4,233,972 A    11/1980 Hauff et al.
(Continued)

FOREIGN PATENT DOCUMENTS

CN    1805766 A    7/2006
CN    1859940 A    11/2006
(Continued)

OTHER PUBLICATIONS

Office Action dated Dec. 26, 2017 issued in Japanese Application No. 2014-78423 with English translation (5 pages).
(Continued)

*Primary Examiner* — Annette Dixon
(74) *Attorney, Agent, or Firm* — Nixon & Vanderhye P.C.

(57) ABSTRACT

A head-mountable flow generator is configured to deliver a flow of breathable gas at a continuously positive pressure with respect to ambient air pressure to a patient interface in communication with an entrance to a patient's airways including at least an entrance of the patient's nares, while the patient is sleeping, to ameliorate sleep disordered breathing. The flow generator includes a motor, an impeller assembly and housing that encases the motor and the impeller assembly. The housing is configured to be mounted on the patient's head and comprises an inlet to receive the flow of breathable gas and a pair of opposing outlets to deliver the flow of breathable gas. In addition, the impeller assembly is configured to pressurize the flow of breathable gas received from the inlet, and the housing is configured to convey the pressurized flow of breathable gas through both outlets.

28 Claims, 15 Drawing Sheets

Related U.S. Application Data continuation of application No. 12/362,817, filed on Jan. 30, 2009, now Pat. No. 8,667,962.

(60) Provisional application No. 61/024,993, filed on Jan. 31, 2008.

(51) Int. Cl.

| | | |
|---|---|---|
| *F04D 17/16* | (2006.01) | |
| *F04D 29/66* | (2006.01) | |
| *A61M 16/08* | (2006.01) | |
| *F04D 17/12* | (2006.01) | |
| *F04D 25/06* | (2006.01) | |
| *F04D 27/00* | (2006.01) | |
| *F04D 29/28* | (2006.01) | |
| *F04D 29/42* | (2006.01) | |

(52) U.S. Cl.
CPC ........ *A61M 16/06* (2013.01); *A61M 16/0666* (2013.01); *A61M 16/0683* (2013.01); *A61M 16/0694* (2014.02); *A61M 16/0816* (2013.01); *A61M 16/0875* (2013.01); *F04D 17/12* (2013.01); *F04D 17/164* (2013.01); *F04D 25/0673* (2013.01); *F04D 27/004* (2013.01); *F04D 29/281* (2013.01); *F04D 29/4206* (2013.01); *F04D 29/664* (2013.01); *A61M 2205/42* (2013.01); *A61M 2205/8206* (2013.01); *A61M 2205/8237* (2013.01); *A61M 2209/086* (2013.01); *A61M 2209/088* (2013.01)

(58) Field of Classification Search
CPC .............. A61M 16/107; A61M 16/122; A61M 2202/0208; A61M 2205/3368; A61M 2205/42; B23P 15/00; F01D 5/02; F01D 5/04; F01D 5/045; F01D 5/14; F01D 5/225; F04D 17/00; F04D 17/02; F04D 17/025; F04D 17/12; F04D 17/122; F04D 17/16; F04D 17/164; F04D 25/00; F04D 25/06; F04D 25/0606; F04D 25/082; F04D 25/12; F04D 25/16; F04D 25/166; F04D 27/004; F04D 29/046; F04D 29/059; F04D 29/28; F04D 29/281; F04D 29/284; F04D 29/30; F04D 29/4253; F04D 29/44; F04D 29/444; F04D 29/54; F04D 29/582; F04D 29/601; F04D 29/662; F04D 29/666; F04D 29/667; F04D 29/668; H02K 1/185; H02K 15/0435; H02K 2205/09; H02K 5/04; H02K 5/08; H02K 5/128; H02K 5/1732; H02K 5/225; H02K 5/24; H02K 7/083; H02K 7/14; H02K 9/14; Y02T 50/671; Y02T 50/673; Y10T 29/49009; Y10T 29/49329
See application file for complete search history.

(56) References Cited

U.S. PATENT DOCUMENTS

| | | | |
|---|---|---|---|
| 4,297,999 A | 11/1981 | Kitrell | |
| 4,590,951 A | 5/1986 | O'Conner | |
| 4,653,976 A | 3/1987 | Blair et al. | |
| 5,303,701 A | 4/1994 | Heins et al. | |
| 5,318,020 A | 6/1994 | Schegerin | |
| 5,372,130 A | 12/1994 | Stern et al. | |
| 5,538,000 A | 7/1996 | Rudolph | |
| 6,435,184 B1 | 8/2002 | Ho | |
| 6,513,526 B2 | 2/2003 | Kwok et al. | |
| 6,561,190 B1 | 5/2003 | Kwok | |
| 6,561,191 B1 | 5/2003 | Kwok | |
| 6,772,760 B2 | 8/2004 | Frater et al. | |
| 6,772,762 B2 | 8/2004 | Piesinger | |
| 6,889,689 B1 | 5/2005 | Neuman | |
| 6,895,962 B2 | 5/2005 | Kullik et al. | |
| 6,910,483 B2 | 6/2005 | Daly | |
| 7,748,381 B2 | 7/2010 | Croll et al. | |
| 8,297,285 B2 * | 10/2012 | Henry ................... | A61M 16/06 128/207.18 |
| 8,667,962 B2 * | 3/2014 | Kenyon ............ | A61M 16/0057 128/200.24 |
| 9,381,318 B2 * | 7/2016 | Kenyon ............ | A61M 16/0057 |
| 10,137,264 B2 * | 11/2018 | Darby ................ | A61M 16/024 |
| 2001/0014290 A1 * | 8/2001 | Takura .................. | F04D 1/006 417/371 |
| 2002/0029777 A1 | 3/2002 | Zimprich et al. | |
| 2002/0119044 A1 | 8/2002 | O'Connor et al. | |
| 2003/0062045 A1 | 4/2003 | Woodring et al. | |
| 2003/0172930 A1 | 9/2003 | Kullik et al. | |
| 2004/0065330 A1 | 4/2004 | Landis | |
| 2004/0079373 A1 | 4/2004 | Mukaiyama et al. | |
| 2004/0226562 A1 | 11/2004 | Bordewick | |
| 2005/0034724 A1 | 2/2005 | O'Dea | |
| 2005/0103339 A1 | 5/2005 | Daly et al. | |
| 2005/0217673 A1 | 10/2005 | Daly et al. | |
| 2006/0096596 A1 | 5/2006 | Occhialini et al. | |
| 2006/0150973 A1 | 7/2006 | Chalvignac | |
| 2006/0237013 A1 | 10/2006 | Kwok | |
| 2007/0000493 A1 | 1/2007 | Cox | |
| 2007/0089221 A1 | 4/2007 | Manzella et al. | |
| 2007/0251527 A1 | 11/2007 | Sleeper | |
| 2007/0277827 A1 * | 12/2007 | Bordewick ........... | A61M 16/00 128/205.25 |
| 2008/0000474 A1 | 1/2008 | Jochle et al. | |
| 2008/0060649 A1 | 3/2008 | Veliss et al. | |
| 2008/0216831 A1 | 9/2008 | McGinnis et al. | |
| 2008/0216833 A1 | 9/2008 | Pujol et al. | |
| 2008/0304986 A1 | 12/2008 | Kenyon et al. | |
| 2009/0194101 A1 | 8/2009 | Kenyon et al. | |
| 2014/0158134 A1 | 6/2014 | Kenyon et al. | |

FOREIGN PATENT DOCUMENTS

| | | |
|---|---|---|
| DE | 102 61 602 A1 | 7/2004 |
| EP | 0 066 451 A1 | 12/1982 |
| EP | 0 164 946 A2 | 12/1985 |
| EP | 0 528 733 A1 | 2/1993 |
| EP | 1 318 307 A1 | 6/2003 |
| GB | 2 209 474 A | 5/1989 |
| GB | 2209474 | 5/1989 |
| GB | 2 215 216 A | 9/1989 |
| JP | 54-70108 | 10/1952 |
| JP | 58-500551 A | 4/1983 |
| JP | 2005-273617 | 10/2005 |
| JP | 2007-78259 | 3/2007 |
| JP | 2007-506482 | 3/2007 |
| JP | 2009-533153 | 9/2009 |
| JP | 2009-537735 | 10/2009 |
| WO | WO 82/03548 A1 | 10/1982 |
| WO | WO 99/13931 | 3/1999 |
| WO | WO 2004/108198 A1 | 12/2004 |
| WO | WO 2005/028009 A1 | 3/2005 |
| WO | WO 2005/063328 A1 | 7/2005 |
| WO | WO 2007/048205 A1 | 5/2007 |
| WO | WO 2007/048206 A1 | 5/2007 |
| WO | WO 2007/117716 A2 | 10/2007 |
| WO | WO 2007/134405 A1 | 11/2007 |
| WO | WO 2008/028247 A1 | 3/2008 |

OTHER PUBLICATIONS

Notification of Reexamination dated Sep. 20, 2017 issued in Chinese Application No. 201410466771.X (17 pages).
Office Action dated Feb. 4, 2017 issued in Chinese Application No. 201410466771.X with English translation (13 pages).
Extended European Search Report dated Feb. 13, 2018 issued in European Application No. 17181906.3 (6 pages).

(56) References Cited

OTHER PUBLICATIONS

Decision of Rejection dated Jan. 18, 2016 issued in Japanese Application No. 2014-078423 with English translation (12 pages).
Decision of Reexamination dated Dec. 29, 2015 issued in Chinese Application No. 200910126785.6 with English translation (34 pages).
Notification of the First Office Action dated Jan. 5, 2016 issued in Chinese Application No. 201410466771.X with English language translation (18 pages).
Notice of Reasons for Rejection dated Apr. 20, 2015 issued in Japanese Application No. 2014-078423 with English translation (10 pages).
Notice of Reasons for Rejection dated Oct. 28, 2014 issued in Japanese Application No. 2009-020018 with English translation (8 pages).
Patent Examination Report No. 1 dated Jul. 23, 2014 issued in corresponding Australian Application No. 2014200366 (2 pages).
Decision of Rejection dated May 27, 2014 in Chinese Application No. 200910126785.6 (14 pages).
Notification of the Third Office Action dated Nov. 5, 2013 in Chinese Application No. 200910126785.6, with English Translation (13 pages).
Patent Examination Report No. 2 issued Aug. 28, 2013 in Australian Application No. 2009200357 (3 pages).
Notification of the Second Office Action dated Apr. 19, 2013 in Chinese Application No. 200910126785.6, with English Translation (14 pages).
Notice of Reasons for Rejection dated Mar. 19, 2013 in Japanese Application No. 2009-020018, with English translation (9 pages).
Notification of First Office Action dated Aug. 2, 2012 in Chinese Application No. 200910126785.6, with English Translation (14 pages).
Patent Examination Report No. 1 dated Jan. 31, 2013 in Australian Application No. 2009200357 (3 pages).
Extended European Search Report dated May 20, 2009 in European Application No. 09001343.4.
U.S. Appl. No. 60/494,119, filed Aug. 2003, Gunaratnam et al.
U.S. Appl. No. 29/274,504, filed Apr. 2007, Kenyon.
U.S. Appl. No. 29/274,505, filed Apr. 2007, Kenyon.
U.S. Appl. No. 29/274,506, filed Apr. 2007, Kenyon.
Notification of the Second Office Action dated Aug. 3, 2016 issued in Chinese Application No. 201410466771.X with English translation (13 pages).
Decision of Reexamination dated Jan. 17, 2018 issued in Chinese Application No. 201410466771.X with English translation (25 pages).

* cited by examiner

RESPIRATORY APPARATUS

CROSS REFERENCE TO RELATED APPLICATION

This application is a continuation of U.S. application Ser. No. 14/177,354, filed Feb. 11, 2014, now allowed, which is a continuation of U.S. application Ser. No. 12/362,817, filed Jan. 30, 2009, now U.S. Pat. No. 8,667,962, which claims priority to U.S. application Ser. No. 61/024,993, filed Jan. 31, 2008, the entire contents of each of which are incorporated herein by reference.

INCORPORATION BY REFERENCE

The entire contents of WO 2008/028247 A1, are incorporated herein by reference.

FIELD OF THE INVENTION

The present invention relates to a respiratory apparatus for delivering a flow of pressurized breathable gas to a patient.

BACKGROUND OF THE INVENTION

Obstructive Sleep Apnea (OSA) is a sleep breathing disorder (SBD). For those who have OSA, when they sleep the soft tissue in their throat and airway relax and collapse thus blocking the airway and preventing airflow to the lungs. This cessation of breathing, known as an apnea, can last for up to one minute before the blood oxygen levels reach a critical point where the patient has an arousal and their airway reopens. Most OSA suffers do not remember these arousals, however each arousal places extra strain on a patient's heart and destroys the quality of their sleep.

The treatment for OSA may include continuous positive airway pressure (CPAP). CPAP involves the patient wearing a nasal or facemask that delivers positive pressure into the patient's airway. This acts as a pneumatic splint and holds the patient's airway open to prevent apneas.

A typical respiratory apparatus for CPAP therapy includes a flow generator, including for example an air blower, that generates a flow of pressurized breathable gas, e.g. air, to a patient interface configured to be worn by the patient in sealing engagement with the patient's face. The patient interface may be, for example, a nasal mask, a full face mask, or nasal pillows. The flow generator and the patient interface are connected by a tube that delivers the flow to the patient interface.

The typical respiratory apparatus for CPAP therapy has several disadvantages. The patient interface and tube tend to be bulky, and the tube may be rather long, e.g. from about 2-3 m in length. The headgear used to maintain the patient interface in contact with the patient's face may also be bulky and/or complicated to correctly put on and/or adjust. These factors may make a patient reluctant to start CPAP therapy. These factors may also make it difficult for the patient to find a comfortable sleeping position. During sleep, the patient may change position, and the tube may exert a force, i.e. tube drag, on the patient interface which may disrupt the seal between the patient interface and the patient's face. This may result in a leak in the patient interface, which reduces the efficacy of the treatment. Leakage from the patient interface may also irritate the patient, or the patient's sleeping partner, thus further damaging the quality of the patient's sleep.

Patients using a typical CPAP apparatus for therapy may also find it difficult to travel with the apparatus. The flow generator, tube, and mask may be difficult to pack in luggage, and may take up a lot of room within the luggage. The patient may also find it difficult to use the apparatus away from home as the flow generator typically includes a power cord that must be plugged into a power source, e.g. an AC wall socket, which may not be accessible, or available, at the location the patient is visiting.

SUMMARY

One aspect relates to enhancing the treatment delivery by a device that incorporates all, or most, of the components of a CPAP system into a single wearable device. For example, the mask and flow generator may be integrated into a mask system worn by the patient. The flow generator may be incorporated into a headgear configured to support the mask. This aspect provides several advantages over current CPAP systems.

Another aspect relates to providing a CPAP system that is streamlined, for example by the removal of the flow generator power cable and/or the air delivery tube. According to this aspect, the patient has increased freedom of movement, including during sleep. The elimination of the tube may lead to reduction in leaks due to a reduction in destabilizing forces on the patient interface.

Yet another aspect relates to reducing the size of a blower in a flow generator blower assembly as a result of lower power requirements, which are possible due to the reduction, or elimination, of head loss in the flow in an air delivery tube.

A further aspect relates to a CPAP system that is less obtrusive and more intuitive to use for the patient. The CPAP system may be anthropometrically designed to engage the wearer's head and face in a manner readily and easily understood by the patient.

An even further aspect relates to a CPAP system that is portable and may be used by the patient when away from home. The CPAP system may be configured to contain its own power supply, e.g. a battery or battery pack. The CPAP system may also be configured to be received in a docking station to recharge the power supply.

Still another aspect relates to a flow generator that is reduced in size compared with stand alone flow generators. The flow generator may be incorporated into a housing that is configured to engage the patient's head. Such a flow generator may operate on a rechargeable power supply, e.g. a battery or battery pack, for the entirety of the patient's sleep cycle. The flow generator may also generate less noise, and be more efficient, than stand alone flow generators.

According to a sample embodiment, a flow generator for generating a flow of pressurized breathable gas comprises a cylindrical housing; a motor supported in the housing, the motor having a shaft having a first end and a second end opposite the first end, the shaft being generally coincident with an axis of the motor; a first impeller attached to the first end of the shaft; a second impeller attached to the second end of the shaft; and a stator that directs an air flow from the first impeller back towards the motor axis. The housing comprises an inlet adjacent the first end of the shaft and having an inlet axis generally coincident with the motor axis, and at least one outlet between the first and second impellers, the at least one outlet having an outlet axis generally tangential to a circumference of the cylindrical housing.

According to another sample embodiment, an apparatus for delivering a flow of pressurized breathable gas to a patient comprises a flow generator, for example as discussed in the preceding paragraph, and a casing to contain the flow generator. The apparatus further comprises a power supply for the flow generator; at least one delivery conduit to convey the flow of pressurized breathable gas; and a patient interface to receive the flow of pressurized breathable gas from the at least one delivery conduit and deliver it to the patient's airways.

Other aspects, features, and advantages will become apparent from the following detailed description when taken in conjunction with the accompanying drawings, which are a part of this disclosure and which illustrate, by way of example, principles of the invention.

BRIEF DESCRIPTION OF THE DRAWINGS

The accompanying drawings facilitate an understanding of the various embodiments described herein. In such drawings:

FIG. 9b schematically illustrates an exploded assembly view of the blower assembly of FIG. 9a;

DETAILED DESCRIPTION OF ILLUSTRATED EMBODIMENTS

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

Respiratory Apparatus First Embodiment

Figure 1:
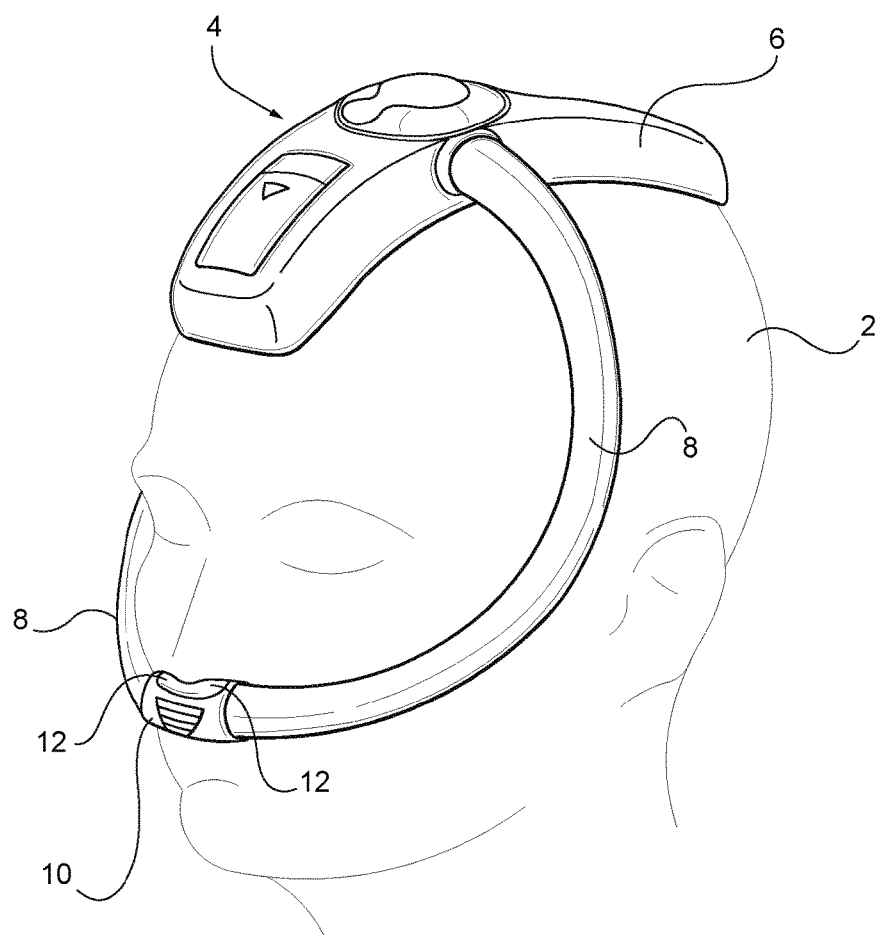
FIG. 1 schematically illustrates a respiratory apparatus according to a sample embodiment.

Referring to FIG. 1, a respiratory apparatus for delivering a flow of pressurized breathable gas to a patient 2, for example to treat SBD, such as OSA, comprises a flow generator 4 to generate the flow of pressurized breathable gas. The flow generator 4 is contained in a flow generator housing or casing 6 that is anthropometrically configured to engage the head of the patient 2. As shown in FIG. 1, the flow generator housing 6 is configured to engage the top of the patient's head to permit the patient to sleep on the patient's side without disturbing the positioning of the flow generator housing 6. As shown in FIG. 1, the flow generator housing may have a curvature in the back to front direction of the housing, and a curvature in a lateral direction, i.e. in a direction from one side of the patient's head to the other side.

The flow generator 4 delivers a flow of pressurized breathable gas through delivery tubes or conduits 8 which are connected to the flow generator housing 6 for receipt of the flow of pressurized breathable gas. The flow of pressurized breathable gas is delivered by the delivery conduits 8, which extend from the flow generator housing 6 along the sides of the face of the patient 2, to a patient interface 10 that is in contact with the nasal passageways of the patient 2. As shown in FIG. 1, the patient interface 10 may support nasal pillows or prongs 12 which are in sealing contact with the nares of the patient's nose. It should be appreciated, however, that the delivery conduits 8 may deliver the flow of pressurized breathable gas to a nasal mask which covers only the nose of the patient. As another example, the delivery conduits 8 may be connected to a full face mask which covers the nose and mouth of the patient. As an even further example, the delivery conduits 8 may be connected to a patient interface that includes a mouth covering portion having nasal pillows or prongs extending from the mouth covering portion for sealing engagement with the nose of the patient. It should be even further appreciated that the patient interface may include nasal cannulae which do not sealingly engage with the nose of the patient.

The conduits 8 may be formed of soft material, for example silicone rubber, to isolate vibrations from the flow generator 4. The conduits 8 may also be connected to the flow generator by a connector configured to isolate vibrations, for example a soft grommet or a bellows type connector. The conduits 8 may also be the conduits as disclosed in U.S. Patent Application Publication 2008/0060649 A1, the entire contents being incorporated herein by reference.

Respiratory Apparatus Second Embodiment

Figure 2:
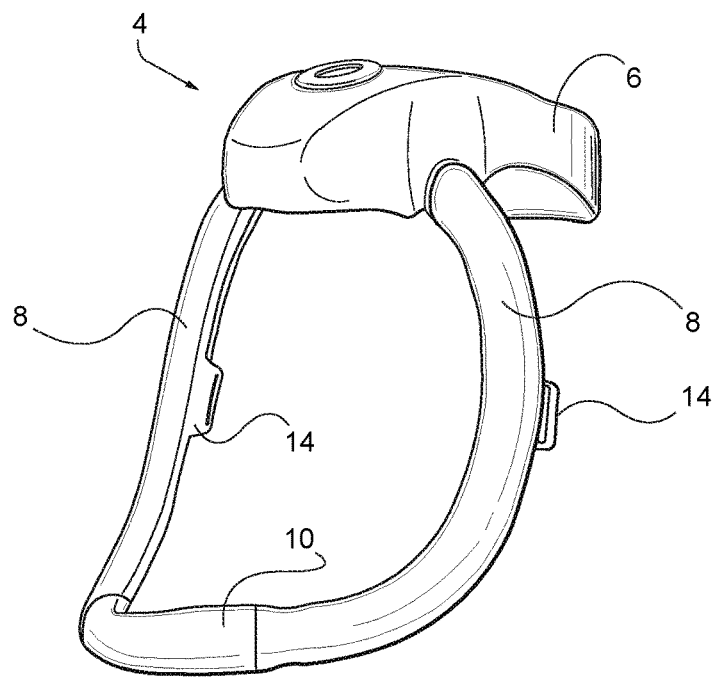
FIG. 2 schematically illustrates a respiratory apparatus according to another sample embodiment.

Referring to FIG. 2, a respiratory apparatus according to another sample embodiment includes strap attachment portions 14 provided on the delivery conduits 8. A strap, or headgear system, may be connected to the strap attachment portions to provide additional securement of the respiratory apparatus to the head of the patient. As shown in FIG. 2, the flow generator housing 6 may be configured to extend towards the back of the head of the patient 2, but may not extend as far forward on the head of the patient 2 as the flow generator housing 6 of the sample embodiment of FIG. 1.

Figure 3:
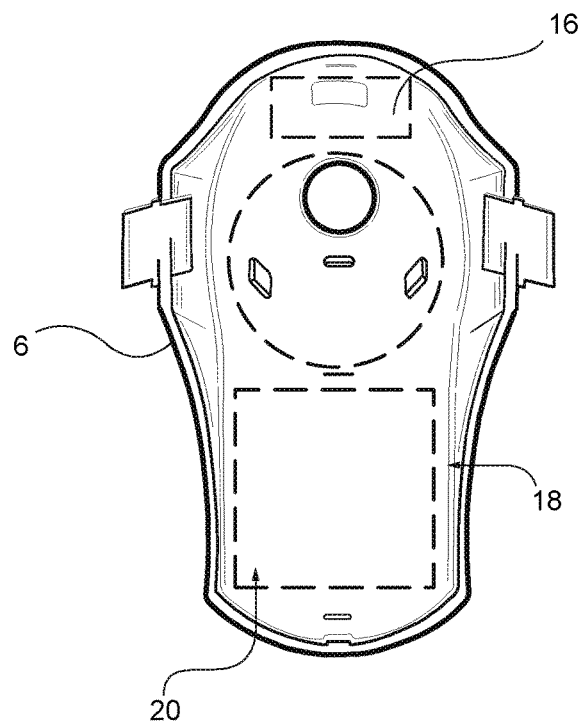
FIG. 3 schematically illustrates a flow generator housing or casing for a respiratory apparatus according to a sample embodiment.

Referring to FIG. 3, the flow generator housing 6 may be configured to support a voltage regulator 16, a motor controller 18 and a power source 20. The power source 20 may comprise a battery, or a plurality of batteries. For example, the battery or batteries may be configured as lithium polymer batteries having a volumetric energy density of about 250-530 Wh/L, for example about 270 to 400 Wh/l, as another example about 330 Wh/l and a gravimetric energy density of about 150-200 Wh/kg, for example about 155 to 175 Wh/kg, as another example about 163 Wh/kg. Such a battery would have, for example, a battery volume of 112 $cm^2$ and a weight of 225 g. The lithium polymer battery may comprise 32 lithium polymer battery cells that would provide approximately 8 hours of power to an electric motor of a blower assembly of the flow generator 4 for generating a flow of about 40-60 l/min, for example, 50 l/min at a pressure in a range of about 2-12 cm $H_2O$, for example about 6 cm $H_2O$. The battery cells may be flexible and thus may be curved for insertion into the housing 6 which may be curved to match the shape of the top of the patient's head.

The lithium polymer battery may have a life cycle of approximately 500 charges. The flow generator housing 6 may be provided with a docking station configured to charge the battery when the housing 6 is placed in the station.

Flow Generator and Blower Assembly

Figure 4:
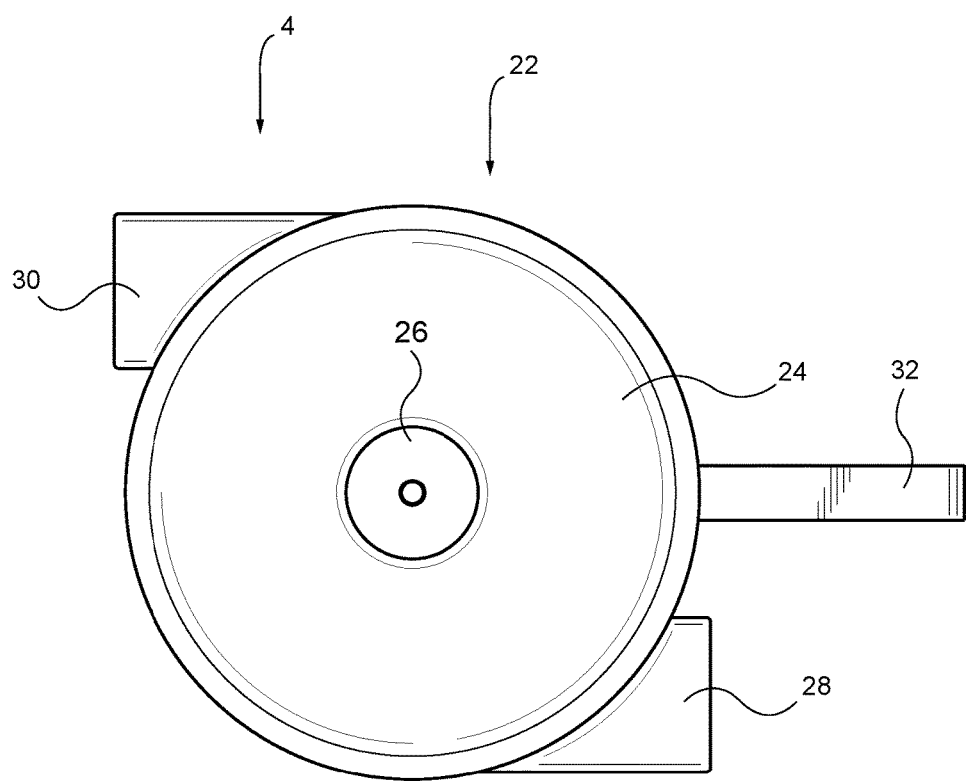
FIG. 4 schematically illustrates a blower assembly of a flow generator for a respiratory apparatus according to a sample embodiment.
Figure 5:
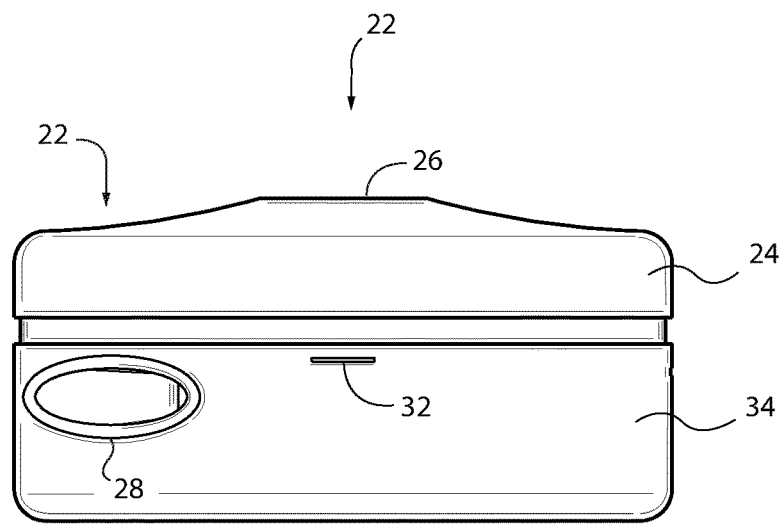
FIG. 5 schematically illustrates a side elevation view of the blower assembly of FIG. 4.
Figure 6:
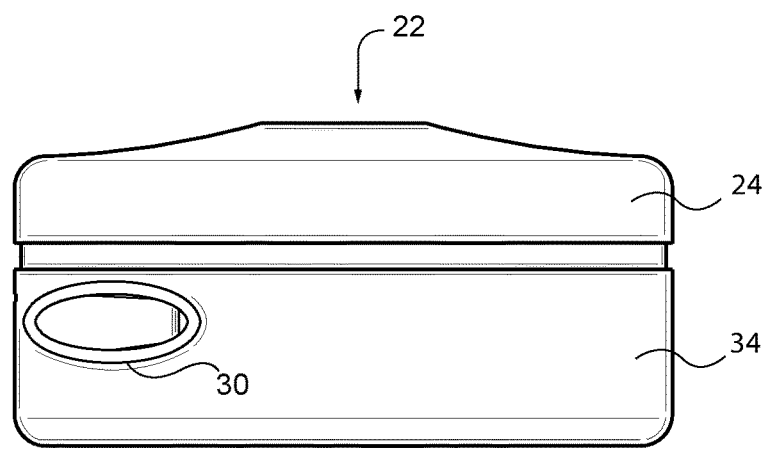
FIG. 6 schematically illustrates an opposite side elevation view of the blower assembly of FIG. 4.
Figure 7:
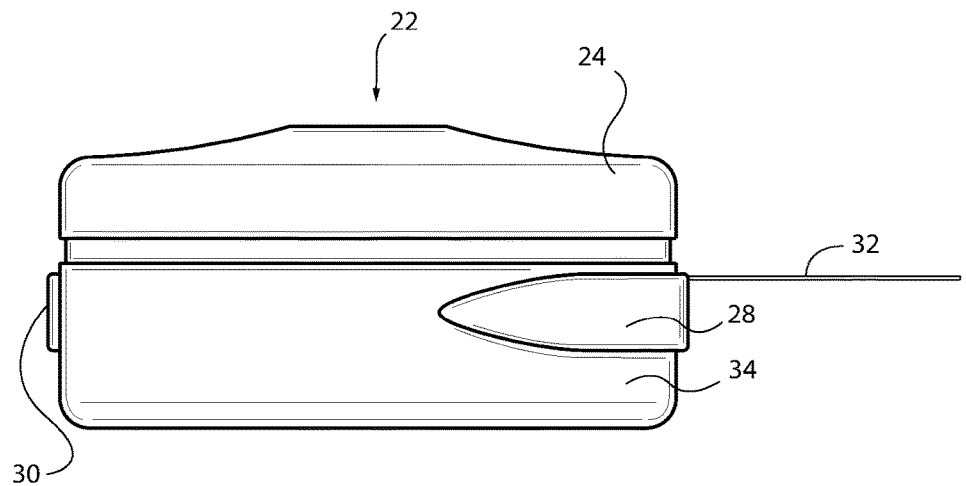
FIG. 7 schematically illustrates a front side election view of the blower assembly of FIG. 4.
Figure 8:
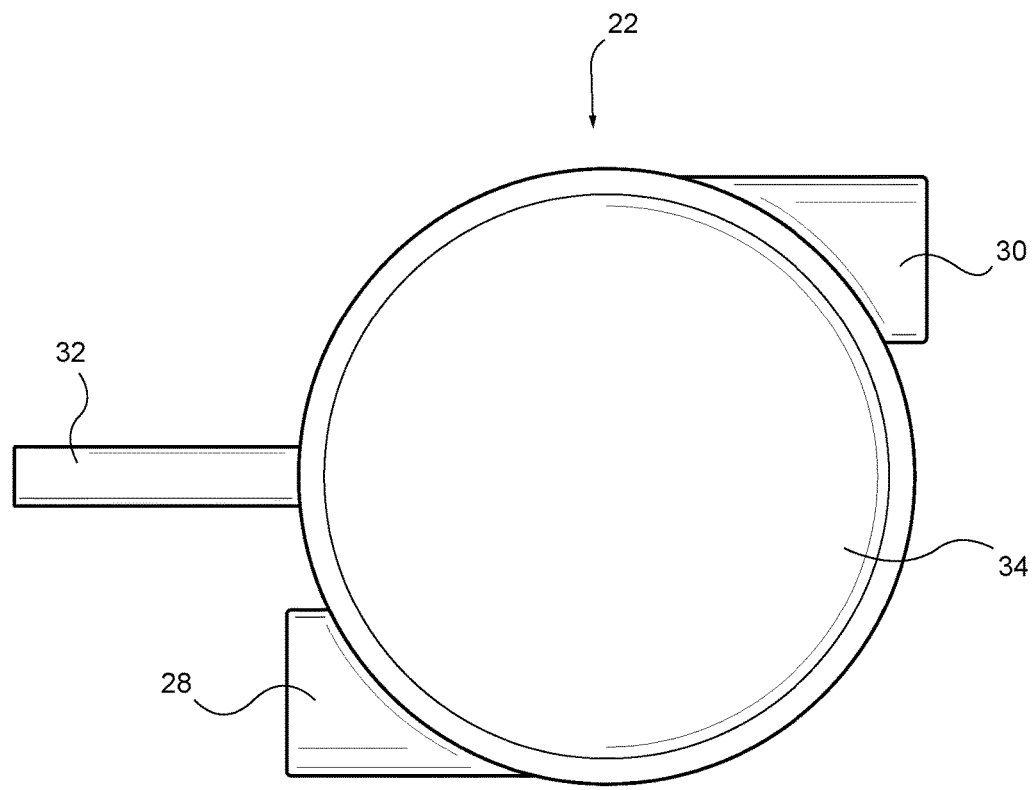
FIG. 8 schematically illustrates a bottom view of the blower assembly of FIG. 4.

Referring to FIGS. 4 and 5, the flow generator 4 comprises a blower assembly 22. The blower assembly 22 comprises a blower assembly upper housing 24 and a blower assembly lower housing 34. A blower assembly inlet 26 is provided in the upper housing 24. It should be appreciated that the use of the terms "upper" and "lower" refer to the orientation of the blower assembly housing shown in the drawings and not necessarily to any required orientation of the blower assembly. As shown in FIGS. 4-9b, the blower assembly 22 comprises a first outlet 28 and a second outlet 30 on opposite sides of the lower housing 34. An electrical connector 32 is provided between the upper housing 24 and the lower housing 34 to provide power to an electric motor 44 (FIG. 10).

Figure 10:
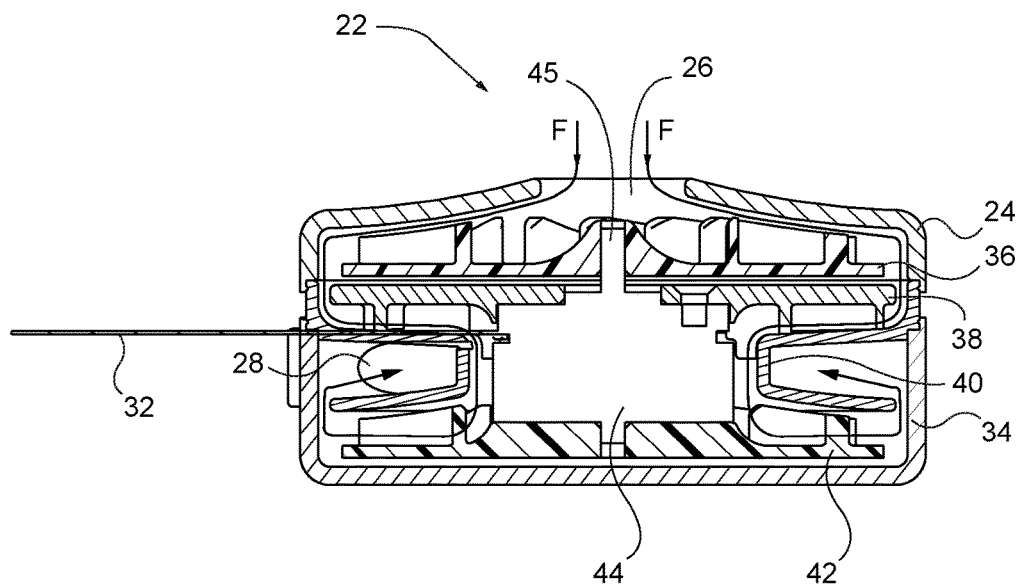
FIG. 10 schematically illustrates a cross-section of the blower assembly of FIG. 4.

Referring to FIG. 10, the blower assembly 22 comprises the upper housing 24 and the lower housing 34 and a middle housing 40 provided between the upper housing 24 and the lower housing 34. A stator 38 is supported on the middle housing 40. The electric motor 44 is supported by the stator 38.

The electric motor 44 includes a shaft 45 that extends from opposite sides of the electric motor 44. The shaft 45 may be generally coincident with an axis of the motor 44. A first impeller 36 is connected to the shaft 45 for rotation with the shaft upon actuation of the electric motor 44. A second impeller 42 is connected to the opposite side of the shaft 45 and thus the opposite side of the motor for rotation with the shaft 45 upon actuation of the electric motor 44. The motor 44 may be selected from a variety of commercially available motors, for example from the motors supplied by Maxon Motor of Switzerland.

Figure 11:
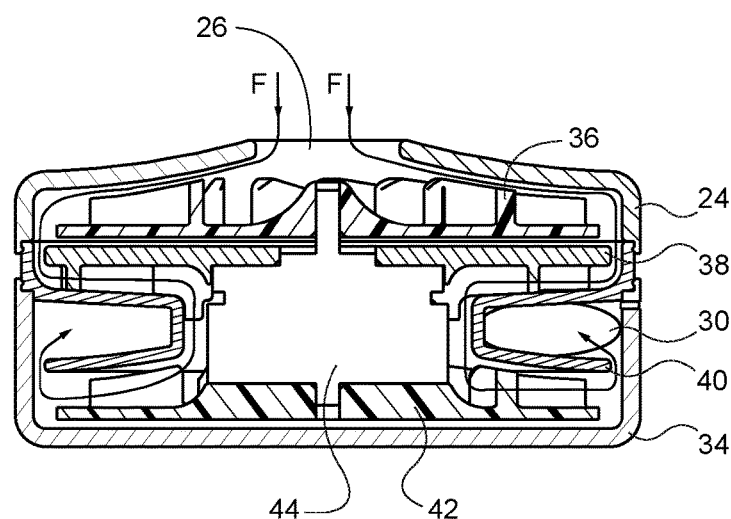
FIG. 11 schematically illustrates a cross-section of the blower assembly of FIG. 4.

Upon actuation of the electric motor 44, the shaft 45 rotates and causes rotation of the first impeller 36 and the second impeller 42. As shown in FIGS. 10 and 11, rotation of the impellers 36, 42 causes a flow F of air into the inlet 26 of the blower assembly 22. The flow enters the upper housing 24 through the inlet 26 and proceeds around the first impeller 36 and is forced down towards the stator 38. The flow then flows around the stator 38 and is forced down through the middle of the second housing 40 towards the second impeller 42. The second impeller 42 forces the flow back up over the periphery of the middle housing 40 and out through the first outlet 28 and the second outlet 30.

The inlet 26 of the blower assembly 22 has an axis that is generally coincident with the axis of the electric motor 44. The axis of the first outlet 28 and the axis of the second outlet 30 are generally tangential to circumference of the housings 24, 34 and generally perpendicular to the axis of the blower assembly 22 and/or the motor 44. The use of the axially coincident inlet 26, the tangential outlets 28, 30, and the two impellers 36, 42 provides a flow path that is folded back on itself, as shown in FIGS. 10 and 11, which utilizes what would otherwise be dead space in the blower assembly and thus reduces the overall size of the blower assembly 22. The reduced size of the blower assembly 22 provides smaller gaps and apertures along the flow path which reduces, or eliminates, turbulence and noise, and enables a low flow Reynolds number for the flow F from the blower assembly 22. The blower assembly 22 may be adapted such that the path of the flow F extends along a first section from the inlet 26 having an axis that is generally parallel and/or coincident to the axis of the electric motor 44. The flow F is then directed, along a second section, radially outwardly with regard to the axis of the electric motor 44 by the first impeller 36. The flow F then extends along a third section, from the outer circumference of the first impeller 36 in a generally axial direction, and generally parallel and in the same general direction as the flow's initial direction when entering the inlet 26 along the first section. The flow F then extends, along a fourth section, radially inwardly along the stator 38. Accordingly, the flow F is folded back on itself at least once, for example from a radial outward direction around the circumference of the first impeller 36 along the second section to a radial inward direction along the fourth section.

The flow F extends radially inwardly along the stator 38 generally up to the outer circumference of the motor 44. The flow F then extends along a fifth section that extends generally axially with respect to the axis of the motor 44 and along the motor in generally the same direction as the first section. The fifth section of the flow F may be defined between the motor 44 and the inner circumference of the middle housing 40. The flow F then extends a long a sixth section and is directed radially outwardly with respect to the axis of the motor 44 by the second impeller 42. Accordingly, the flow F is folded back on itself at least once, and possibly a second time, i.e. from a radial inward direction along stator 38 and along the fourth section to a radial outward direction along the second impeller 42 and the sixth section. At the outer circumferential end of the second impeller 42 the flow F extends, along a seventh section, generally axially upwardly towards the first and/or second outlet 28, 30. Thus the flow F is folded back on itself at least once, and possibly three times. The flow path F may be meandering. It should be appreciated that the description of the flow F relates to the cross sectional views shown in FIGS. 10 and 11. As shown, the flow F may be generally radially symmetrical.

The outlets 28, 30 may be elliptical or oval. The use of elliptical or oval outlets reduces, or minimizes, the size of the outlets and allows the axial dimension, i.e. height, of the blower assembly 22 to be reduced, or minimized. The use of elliptical or oval outlets provides a sufficient cross sectional area to permit the flow to exit the blower assembly and also reduces sharp corners in the blower assembly. As shown, for example in FIGS. 4, 8, 9a, and 9b, there are two outlets 28, 30 symmetrically provided on the blower assembly 22. The use of two symmetrical outlets provides more outlet flow area for a given axial height than a single outlet, and lowers conducted noise. It should be appreciated that more than two outlets may be provided. It should also be appreciated that the outlets may have a 360° rotational symmetry.

Figure 12:
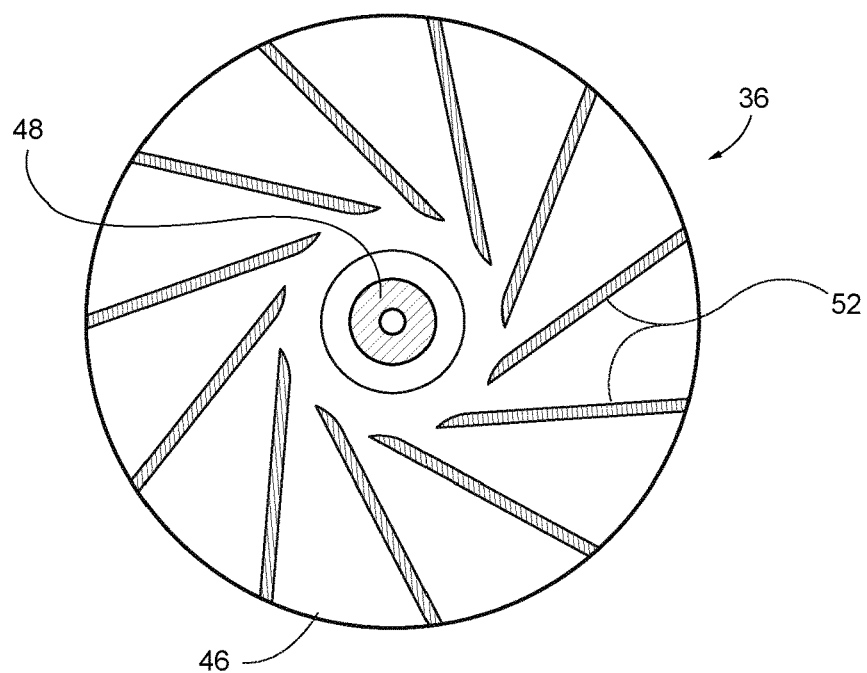
FIG. 12 schematically illustrates a cross-section of a first impeller of the blower assembly of FIG. 4.
Figure 13:
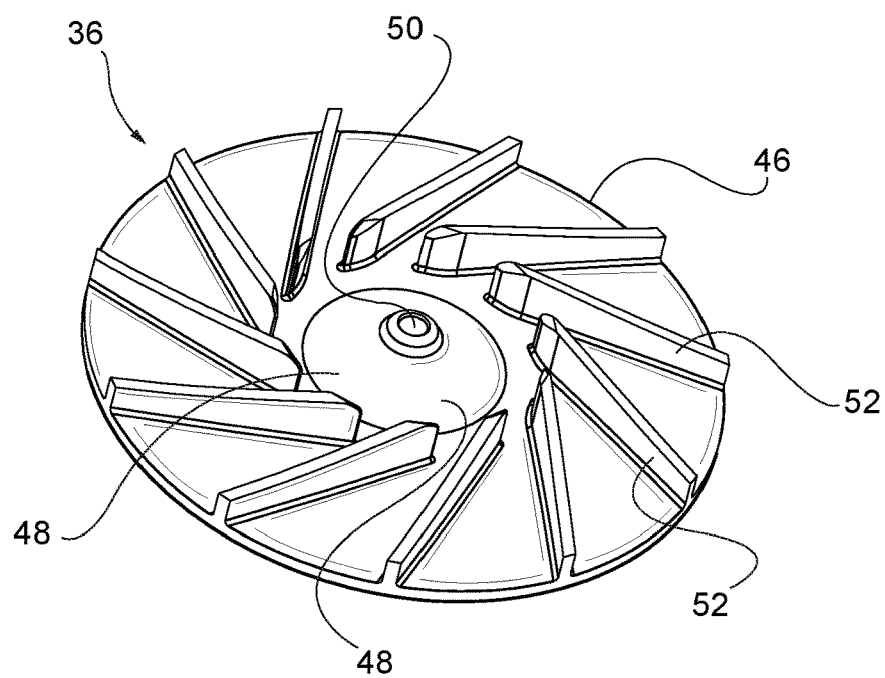
FIG. 13 schematically illustrates a perspective view of the first impeller of FIG. 12.

Referring to FIG. 12, the first impeller 36 includes a first impeller disk 46. A motor mounting portion 48 is configured for mounting the first impeller 36 to the electric motor shaft 45. As shown in FIG. 13, the motor mounting portion 48 includes an aperture 50 configured to receive the electric motor shaft 45. A plurality of vanes 52 are provided on the first impeller disk 46 to generate the flow F upon rotation of the first impeller 36. The vanes 52 direct the flow radially to the periphery of the first impeller 36 as shown in FIGS. 10 and 11. The first impeller 36 generates a flow F that is initially in the axial direction of the electric motor 44.

As shown in FIG. 13, the vanes 52 of the first impeller 36 are generally straight. However, it should be appreciated that the vanes 52 may be curved. As also shown in FIG. 13, the vanes 52 may have a varying height. The height of the vanes may be largest toward the center of the first impeller disk 46 and may be smallest at the outer periphery or circumference of the first impeller disk 46. The height of the vanes for 52 may be related to the diameter of the first impeller disk 46 for providing a desired flow. The height of the vanes 52 may be optimized for the selected diameter of the first impeller disk 46 to further reduce the overall size of the blower assembly 22. The vanes 52 may be configured such that the height of the vanes 52 at their tips (i.e. at the circumferential edge of the disk 46) are the minimum height that does not choke the flow F. The "choke" is related to the cylindrical surface of the disk 46 at the circumferential edge, i.e. the outer edges of the vanes 52, and the axial height of the vanes 52 at the circumferential edge of the disk 46. In other words the "choke" is related to a cylinder of diameter equal to the outer diameter of disk 46 and which has an axial dimension (height) equal to the height of the vanes 52 at the periphery of disk 46. The lower the height of the vanes 52, the lower the Reynolds number and therefore the lower the turbulence noise.

Figure 14:
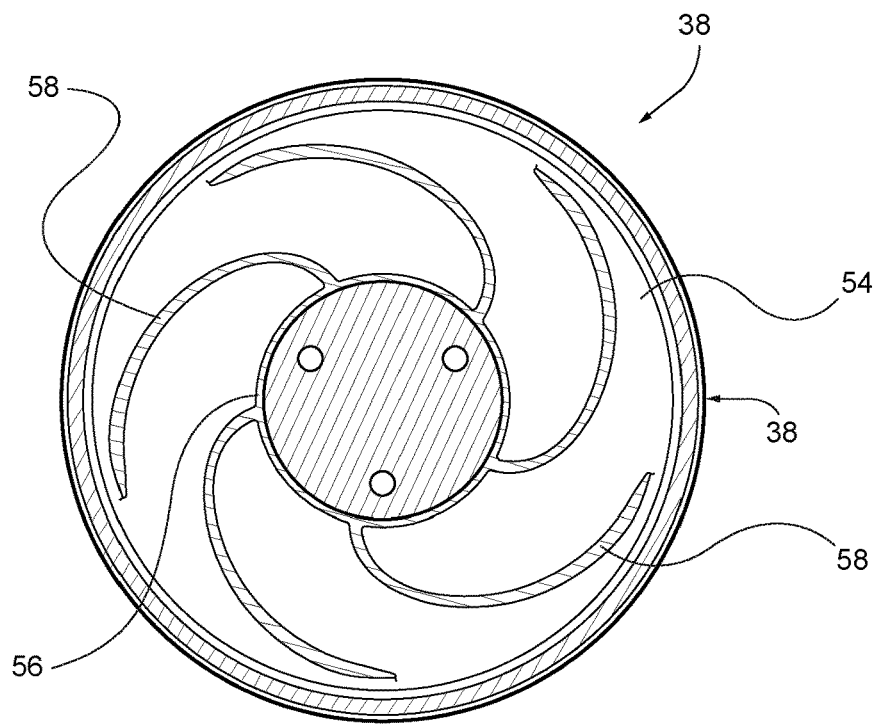
FIG. 14 schematically illustrates a stator of the blower assembly of FIG. 4.

Referring to FIG. 14, the stator 38 comprises a stator disk 54 and a motor mounting portion 56 to mount the stator 38 to the electric motor 44. A plurality of vanes 58 are provided on the stator disk 54. As shown in FIG. 14, the vanes 58 are curved to fold the flow F delivered from the first impeller 36 back towards the center of the blower assembly, i.e. back toward the electric motor 44. The vanes 58 then direct the flow F in the direction of the axis of the electric motor 44 through the middle housing 40 toward the second impeller 42, as shown in FIGS. 10 and 11.

Figure 9A:
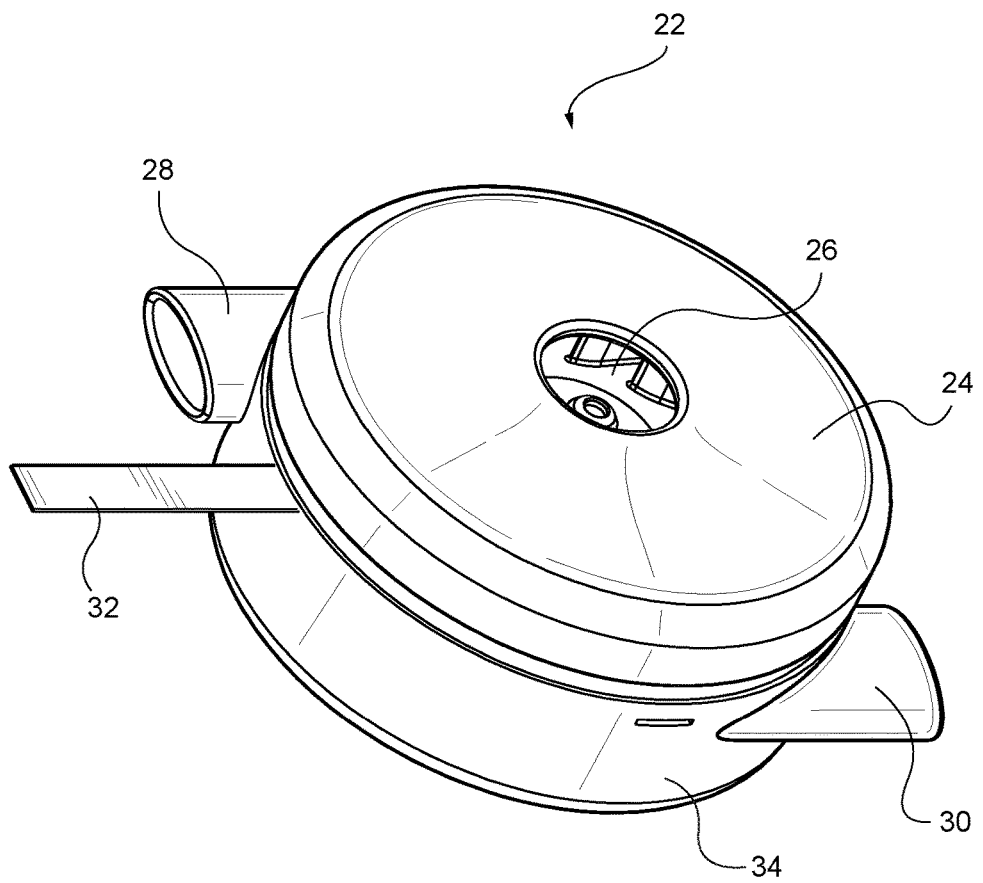
FIG. 9a schematically illustrates a perspective view of the blower assembly of FIG. 4.
Figure 9B:
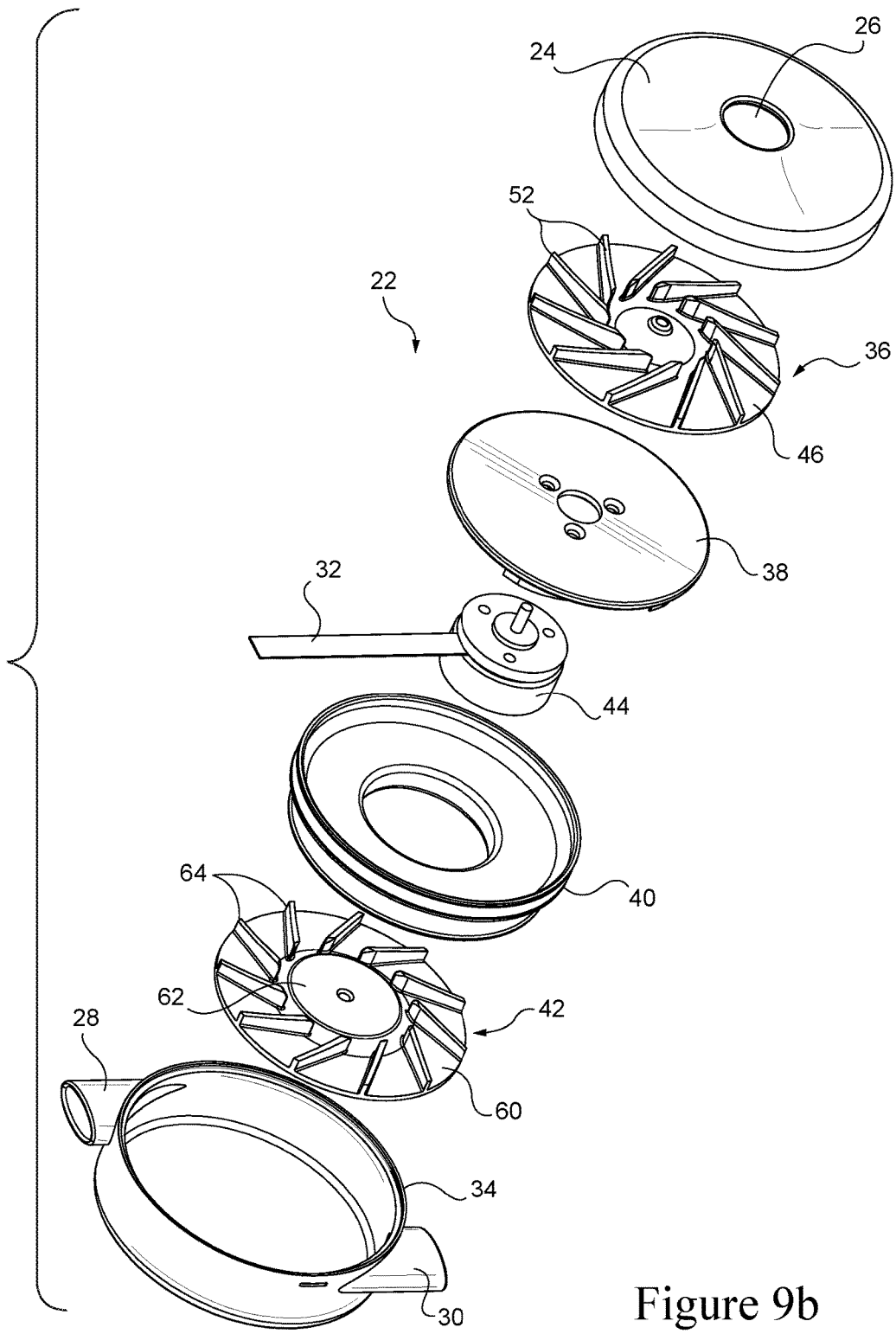
Figure 15:
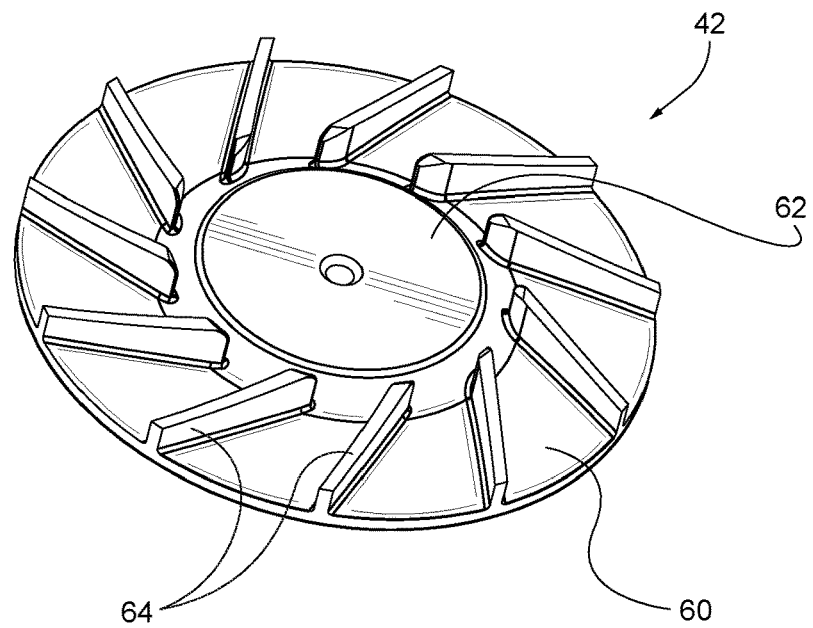
FIG. 15 schematically illustrates a second impeller of the blower assembly of FIG. 4.

Referring to FIG. 15, the second impeller 42 comprises a second impeller disk 60 and a motor mounting portion 62 configured to connect the second impeller 42 to the shaft 45 of the electric motor 44. A plurality of vanes 64 are provided on the second impeller disk 60 for directing the flow F around the middle housing 40 and out the first outlet 28 and a second outlet 30, as shown in FIGS. 10 and 11. By folding the flow F back toward the electric motor 44, and by directing it axially along the circumference of the electric motor 44 before folding the flow F back, radially outwardly be the second impeller 42, the flow F cools the motor 44 and is heated by passing the motor 44. The vanes 64 of the second impeller disk 60 may be configured in a manner similar to the vanes 52 of the first impeller disk 46. As shown in FIGS. 9b, 10 and 11, the inner ends of the vanes 64 define a diameter that is larger than the diameter of the motor 44. This allows the vanes 64 to sit, at least partly, at the same axial position as the lower section of the motor 44, which reduces the axial height of the blower assembly 22.

The blower assembly may have a width of about 45-60 mm, for example about 50-55 mm, as another example about 52 mm, and a height of about 20-30 mm, for example about 23-27 mm, as another example about 25 mm. The motor may have a width of about 15-25 mm, for example about 17-23 mm, as another example about 20 mm, and a height of about 15-20 mm, for example about 17 mm. The motor may be brushless and deliver about 1-5 W shaft power, for example about 3 W. The motor may weigh about 10-20 g, for example about 13-17 g, as another example about 15 g. The blower assembly may provide a flow of about 40-60 l/min, for example about 45-55 l/min, as another example about 50 l/min, at a pressure of about 2-12 cm $H_2O$, for example about 4-8 cm $H_2O$, as another example about 6 cm $H_2O$. It should be appreciated that these flow and pressure ranges are examples and the flow generator may be scaled to provide flow and pressure ranges other than the examples provided herein.

The housing of the blower assembly may be configured to suppress noise generated by the motor 44. For example, a gel layer may be provided between the upper housing 24 and the lower housing 34, and/or a gel layer may be provided between the stator 38 and the motor 44 to damp vibrations and/or noise generated by the motor 44.

Other modifications that may be made to the blower assembly include providing bearings to the housing 24, 34 instead of the motor 44, as disclosed in U.S. Patent Application Publication 2008/0304986 A1, the entire contents of which are incorporated herein by reference, adding a magnet (s) to the impeller(s), and/or configuring the motor as an axial gap motor, for example as disclosed in WO 2007/134405 A1, the entire contents of which are incorporated herein by reference.

It should also be appreciated that other flow generator and blower assemblies may be used in the sample embodiments discussed herein. For example, the flow generator and blower assemblies disclosed in U.S. applications Ser. Nos. 29/274,504, 29/274,505, and 29/274,506, each filed Apr. 27, 2007, and WO 2007/048206 A1, the entire contents of each being incorporated herein by reference, may be used. As another example, the flow generator and blower assemblies disclosed in U.S. applications Ser. Nos. 29/274,504, 29/274, 505, and 29/274,506, filed Apr. 27, 2007, 2006, and WO 2007/048205 A1, the entire contents of which are incorporated herein by reference, may be used.

Respiratory Apparatus Third Embodiment

Figure 16:
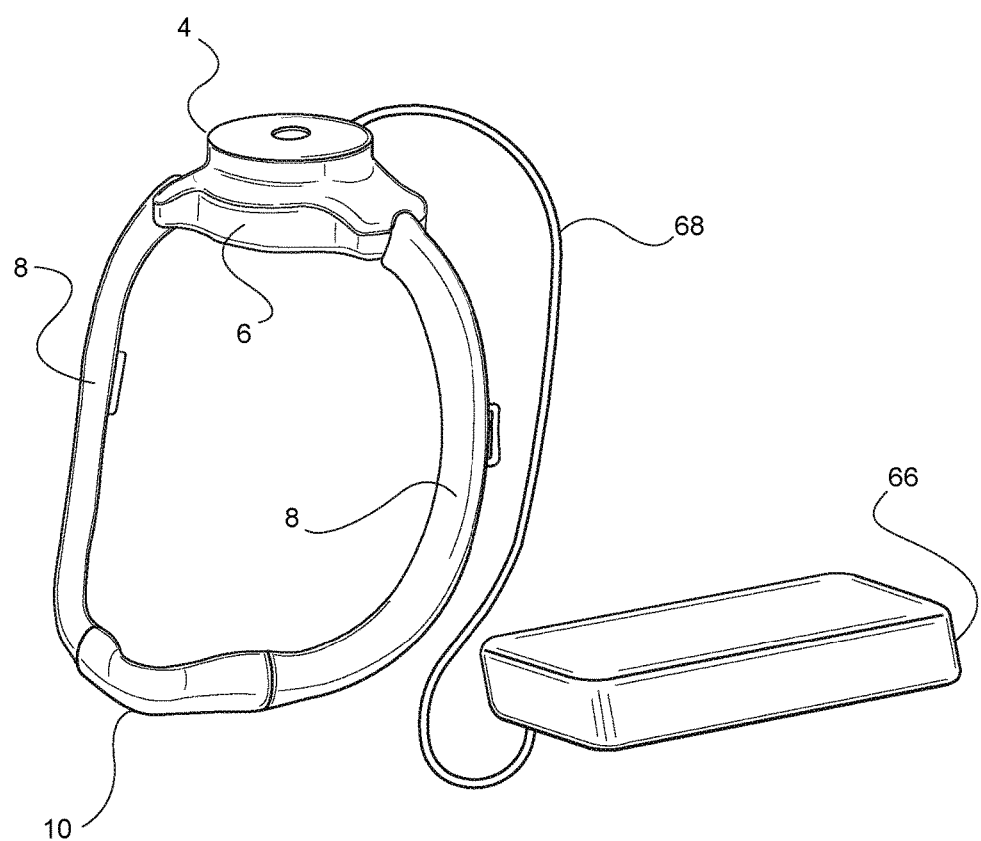
FIG. 16 schematically illustrates a respiratory apparatus according to another sample embodiment.

Referring to FIG. 16, a respiratory apparatus according to another sample embodiment comprises a flow generator 4 provided in a flow generator housing 6 configured to engage the head of the patient, for example the crown of the patient's head. The flow generator 4 is configured to deliver a flow of pressurized breathable gas to delivery conduits 8 which are configured to extend from the flow generator along the sides of the face of the patient to a patient interface 10. The patient interface may include nasal pillows or prongs, a nasal mask, a full face mask, or cannulae.

Power is provided to the flow generator 4 by a power supply and controller 66 that is connected to the flow generator 4 by an electrical connector 68, for example a cable. The power supply/controller 66 may be configured to be docked in a battery charger, or may include an attachment that allows for charging of the power supply and controller from a voltage source, for example a common household 120 volt AC socket, or a 12 volt car battery charging outlet. The remaining configuration and features of the flow generator and blower assembly, respectively, may correspond to those discussed and shown with respect to the preceding and following embodiments.

Respiratory Apparatus Fourth Embodiment

Figure 17:
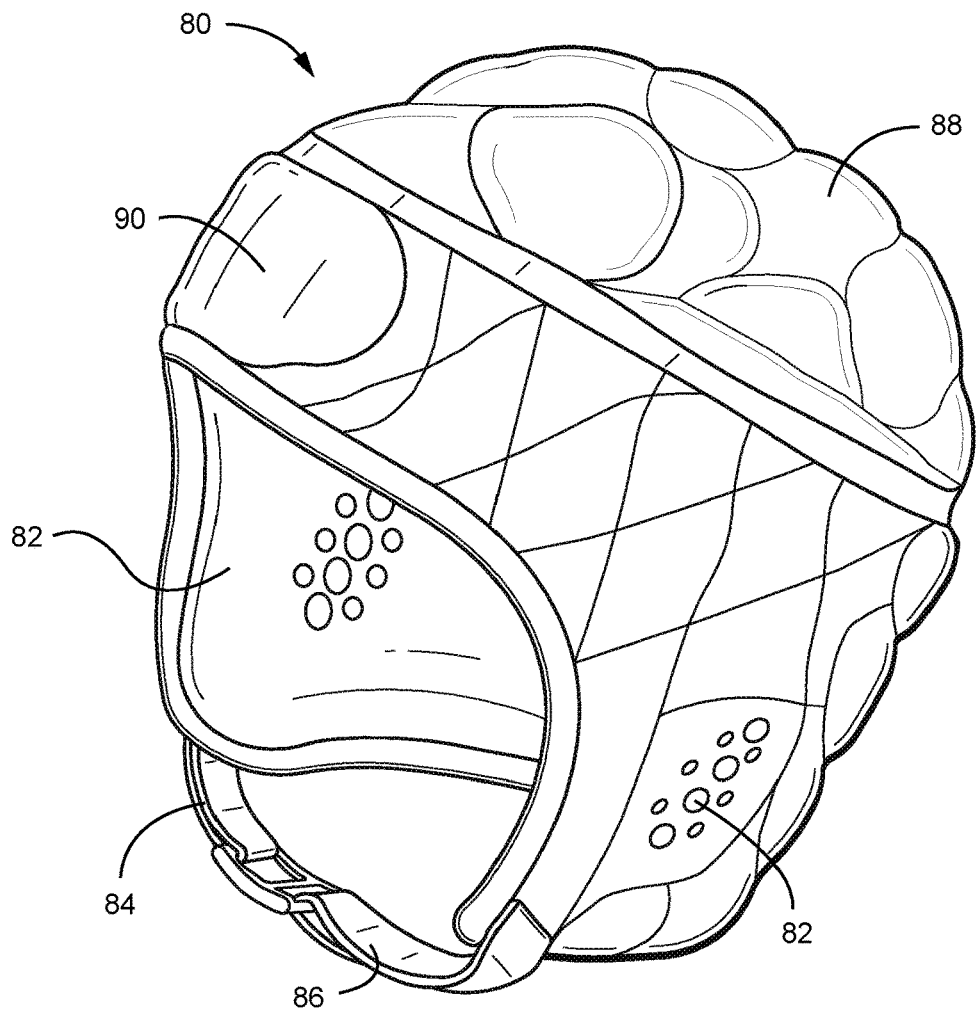
FIG. 17 schematically illustrates a respiratory apparatus according to another sample embodiment.

Referring to FIG. 17, a respiratory apparatus according to another sample embodiment may comprise a headgear 80 that may take the form of, for example, a skull cap. A pair of ear covering portions 82 may be provided as well as a head covering portion 88. A head circling band 90 may be provided between the ear covering portions 82 and the head covering portion 88. A pair of straps, e.g. chin straps, 84, 86 may be provided to the ear covering portions 82 to secure the headgear 80 to the patient.

The flow generator may be provided in the headgear 80, for example in the head covering portion 88. The power supply (e.g. the battery, or batteries, including the flexible cells) and the control electronics (e.g. the voltage regulator and/or the motor controller) may also be provided in the headgear 80, for example in the head covering portion 88 or the ear covering portion(s) 82. The flow generator, the power supply and the control electronics may be encased in foam or other cushioning material to improve the comfort of the headgear. The battery cells may be distributed about the headgear 80 to spread the weight of the power supply throughout the headgear to improve comfort, reduce, or minimize the height of the apparatus, and increase, or maximize, the stability of the apparatus.

Respiratory Apparatus Fifth Embodiment

Figure 18:
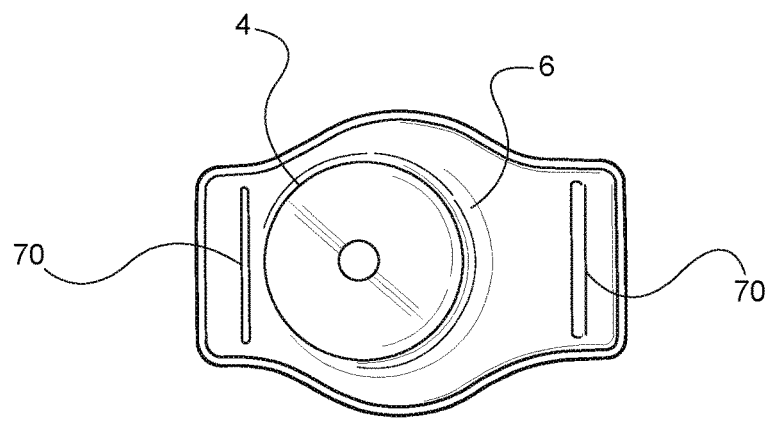
FIG. 18 schematically illustrates a flow generator according to another sample embodiment.
Figure 19:
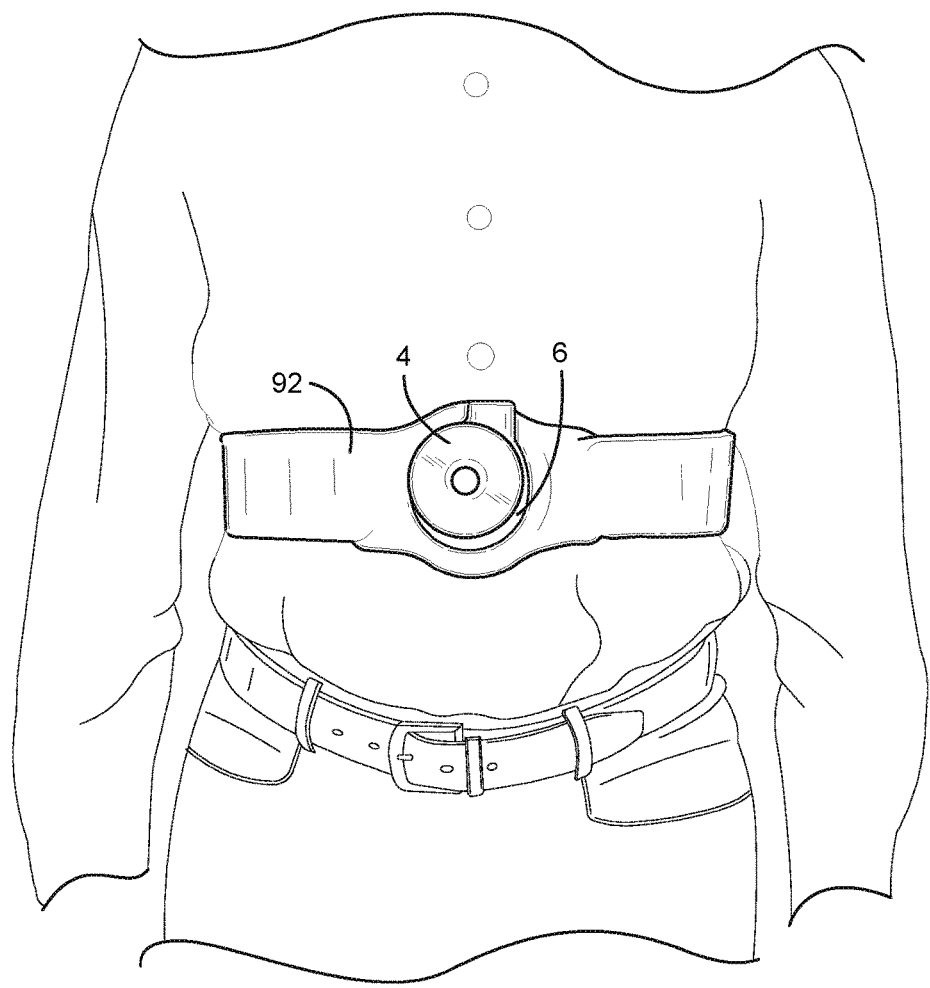
FIGS. 19 and 20 schematically illustrate a respiratory apparatus incorporating the flow generator of FIG. 17.
Figure 20:
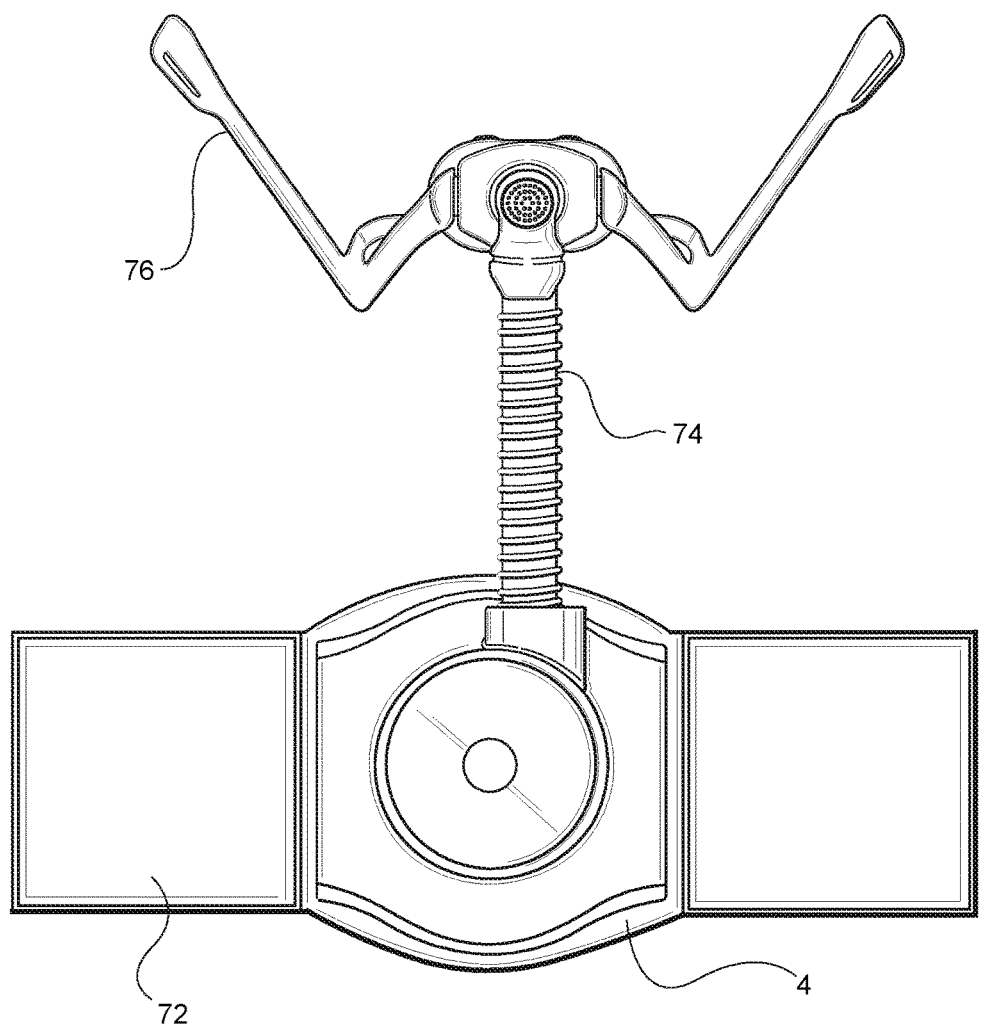

Referring to FIGS. 18-20, a respiratory apparatus according to another sample embodiment comprises a flow generator 4 comprising a flow generator housing or casing 6. The flow generator 4 may include a blower assembly as previously described. The flow generator housing 6 comprises slots 70 configured to receive a band or strap 72 as shown in FIG. 18. The band or strap 72 may be configured to encircle the chest or arm of the patient to support the flow generator 4 at a position spaced from the head of the patient. A delivery tube or conduit 74 is configured to be connected to the flow generator 4 at a first end and configured to be connected to a patient interface 10 at a second end. The delivery tube or conduit 74 may be a retractable tube or conduit that is flexible and extensible to accommodate movement of the patient's head, and thus movement of the patient interface 10. Such a retractable tube is disclosed in U.S. application Ser. No. 12/211,896, filed Sep. 17, 2008, the entire content being incorporated herein by reference. The patient interface may be held in contact with the face of the patient by a headgear system 76.

As shown in FIG. 19, the band, or strap, 92 may be configured to be integrally formed with the flow generator casing 6. Alternatively, the band or strap may be separately formed and passed through the slots 70 in the flow generator casing 6. The respiratory apparatus can be segmented into the respective elements. For example, the power supply (e.g. battery cells or pack) and the control electronics (e.g. the voltage regulator and/or motor controller) may be located to the left and/or right of the flow generator casing 6 and connected by a flexible joint, such as a cable. This permits a more custom fit to the patient.

As shown in FIGS. 19 and 20, the blower assembly housing may differ from the housing disclosed in FIGS. 4-16 in that the blower assembly housing may include a single outlet tangential to the blower assembly inlet. It should be appreciated, however, that the sample embodiment shown in FIGS. 18-20 may be provided with a pair of outlets, and a pair of delivery tubes or conduits which may deliver the flow of pressurized breathable gas to a patient interface having two inlets, for example an inlet on each side of the patient interface. Such a patient interface is disclosed, for example, in WO 2005/063328 A1, assigned to ResMed Ltd.

The flow generator housing 6 may be configured to support the blower assembly 22, the power source 20, e.g. the battery or battery pack, and control circuitry for operation of the electric motor of the blower assembly.

Figure 21:
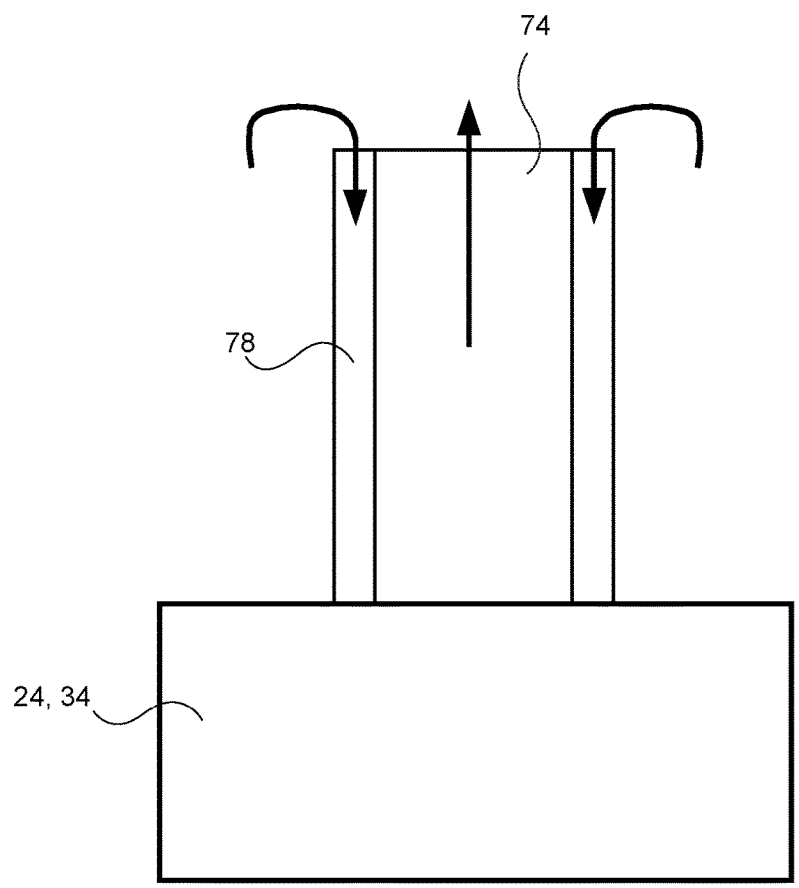
FIG. 21 schematically depicts a respiratory apparatus according to another sample embodiment.

Referring to FIG. 21, a variation of the sample embodiment of FIGS. 18-20 may include a concentric air inlet tube 78 surrounding the air delivery tube 74. If the flow generator is worn beneath the patient's bed clothes, e.g. pyjamas, the concentric air inlet tube may be placed outside the patient's bed clothes to draw fresh air into the flow generator housing.

In the sample embodiments described above, the flow generator may be turned on and off using a switch. It should also be appreciated that the flow generator may be turned on using ResMed's SMART START® control.

Respiratory Apparatus Sound Levels

The sample embodiments of the respiratory apparatus disclosed herein may be configured so that the noise level is sufficiently low to allow patients to sleep. In general, typical flow generators are often configured such that the sound power emitted is about 25 dB based on testing 1 meter away at the front of the device. However, the sample embodiments of the respiratory apparatus disclosed herein are configured to be placed on the user's person, e.g. on the head, an arm, the chest. This proximity of the flow generator to the user may result in an increased sound level experienced by the user, for example by about 10 dB(A). In addition, the sample embodiments disclosed herein may include less insulation around the blower assembly of the flow generator, which may further increase the sound level experienced by the user, for example by about another 10 dB(A). For comparison, a flow generator such as that disclosed in U.S. Patent Application Publication 2008/0304986 A1, the entire contents of which are incorporated herein by reference, comprising no insulation emits about 52 dB(A) sound power when running at 10 cm $H_2O$ air pressure.

The sample embodiments of the respiratory apparatus disclosed herein may comprise insulating material within the headgear, mask, blower assembly, and/or flow generator casing, and/or a muffler, to reduce the sound power emitted. For example, the headgear may be configured to reduce the sound power emitted by about 5-10 dB(A). The sample embodiments of the respiratory apparatus disclosed herein may emit a sound power of between about 10-100 dB(A), for example about 10-65 dB(A), as another example about 10-50 dB(A), as a further example about 20-40 dB(A), and as an even further example less than about 25 dB(A), when the respiratory apparatus is providing a flow at about 10 cm $H_2O$.

In this specification, the word "comprising" is to be understood in its "open" sense, that is, in the sense of "including", and thus not limited to its "closed" sense, that is the sense of "consisting only of." A corresponding meaning is to be attributed to the corresponding words "comprise", "comprised" and "comprises" where they appear.

The term "air" will be taken to include breathable gases, for example air with supplemental oxygen. It is also acknowledged that the blowers described herein may be designed to pump fluids other than air.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment.

Furthermore, each individual component of any given assembly, one or more portions of an individual component of any given assembly, and various combinations of components from one or more embodiments may include one or more ornamental design features. In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability with patients and non-patients alike in non-medical applications.

What is claimed is:

1. A head-mountable flow generator configured to deliver a flow of breathable gas at a continuously positive pressure with respect to ambient air pressure to a patient interface in communication with an entrance to a patient's airways including at least an entrance of the patient's nares, while the patient is sleeping, to ameliorate sleep disordered breathing, the flow generator comprising:
   a motor;
   an impeller assembly configured to be driven by the motor; and
   a housing that encases the motor and the impeller assembly and is configured to be mounted on the patient's head, the housing comprising an inlet configured to receive the flow of breathable gas and a pair of opposing outlets configured to direct the pressurized flow of breathable gas to the patient interface,
   wherein the impeller assembly is configured to pressurize the flow of breathable gas received from the inlet and the housing is configured to convey the pressurized flow of breathable gas through both outlets.

2. The head-mountable flow generator of claim 1, wherein the housing is anthropometrically configured to engage the patient's head.

3. The head-mountable flow generator of claim 1, wherein each of the opposing outlets comprises a connector configured to connect to a respective air delivery tube.

4. The head-mountable flow generator of claim 1, wherein the impeller assembly comprises a first impeller and a second impeller.

5. The head-mountable flow generator of claim 4, wherein the opposing outlets are positioned between the first and second impellers.

6. The head-mountable flow generator of claim 1, wherein each of the pair of opposing outlets is elliptical.

7. The head-mountable flow generator of claim 1, wherein the opposing outlets are symmetrically positioned on the housing.

8. An apparatus for delivering a flow of pressurized breathable gas to a patient and treating a respiratory disorder, the apparatus comprising:
   the flow generator according to claim 1;
   a pair of air delivery conduits, each air delivery conduit being connected to the respective outlet of the flow generator and being configured to convey the pressurized flow of breathable gas from the pair of opposing outlets; and
   the patient interface being adapted to be in communication with an entrance to a patient's airways, the patient interface being configured to be mounted on the patient's face and receive the pressurized flow of breathable gas from the pair of air delivery conduits.

9. The apparatus of claim 8, wherein the pair of air delivery conduits connect to the patient interface at opposite ends of the patient interface.

10. The apparatus of claim 8, wherein each of the pair of air delivery conduits is flexible.

11. A head-mountable flow generator configured to deliver a flow of breathable gas at a continuously positive pressure with respect to ambient air pressure to a patient interface in communication with an entrance to a patient's airways including at least an entrance of the patient's nares, while the patient is sleeping, to ameliorate sleep disordered breathing, the flow generator comprising:
   a motor;
   an impeller assembly configured to be driven by the motor; and
   a housing that encases the motor and the impeller assembly, the housing being configured to be mounted on the patient's head,
   wherein the impeller assembly is configured to pressurize the flow of breathable gas and the housing is configured to direct the pressurized flow of breathable gas out of the flow generator in two distinct flow paths.

12. The head-mountable flow generator of claim 11, wherein the housing is configured so that the pressurized flow of breathable gas exits the housing through outlets on opposite sides of the housing.

13. The head-mountable flow generator of claim 12, wherein the outlets are configured to direct the pressurized breathable gas toward opposite sides of the patient's head when the housing is mounted on the patient's head.

14. The head-mountable flow generator of claim 12, wherein the outlets are elliptical.

15. The head-mountable flow generator of claim 12, wherein the outlets are positioned on the housing to mirror each other.

16. An apparatus for delivering a flow of pressurized breathable gas to a patient and treating a respiratory disorder, the apparatus comprising:
   the flow generator according to claim 11;
   the patient interface being adapted to be in communication with an entrance to a patient's airways, the patient interface being configured to be mounted on the patient's face and receive the pressurized flow of breathable gas from the pair of air delivery conduits; and
   a pair of air delivery conduits, each air delivery conduit being configured to receive a portion of the pressurized flow of breathable gas from the flow generator and convey the pressurized flow of breathable gas to the patient interface.

17. The apparatus of claim 16, wherein the pair of air delivery conduits connect to the patient interface at opposite ends of the patient interface.

18. The apparatus of claim 16, wherein each of the pair of air delivery conduits is flexible.

19. A head-mountable flow generator configured to deliver a flow of breathable gas at a continuously positive pressure with respect to ambient air pressure to a patient interface in communication with an entrance to a patient's airways including at least an entrance of the patient's nares, while the patient is sleeping, to ameliorate sleep disordered breathing, the flow generator comprising:
   a motor;
   an impeller assembly configured to be driven by the motor and pressurize the flow of breathable gas; and
   a housing that encases the motor and the impeller assembly, the housing comprising:
      a bottom surface;
      a top surface opposite the bottom surface, the bottom surface being configured to be closer to the patient's head than the top surface when the flow generator is mounted on the patient's head; and
      a pair of opposing side surfaces extending from the top surface to the bottom surface, each of the side surfaces comprising a distinct outlet configured to receive the pressurized flow of breathable gas from the impeller assembly.

20. The head-mountable flow generator of claim 19, wherein the bottom surface of the housing has a curvature that is aligned in a back to front direction with respect to the patient's head when the housing is mounted on the patient's head.

21. The head-mountable flow generator of claim 19, wherein the bottom surface of the housing has a curvature that is aligned in a lateral direction with respect to the patient's head when the housing is mounted on the patient's head.

22. The head-mountable flow generator of claim 19, wherein the outlets mirror each other.

23. The head-mountable flow generator of claim 19, wherein when the housing is mounted on the patient's head, the opposing side surfaces face opposite sides of the patient's face.

24. The head-mountable flow generator of claim 19, wherein the outlets are configured to direct the pressurized flow of breathable gas toward opposite sides of the patient's face when the housing is mounted on the patient's head.

25. The head-mountable flow generator of claim 19, wherein each outlet is elliptical.

26. An apparatus for delivering a flow of pressurized breathable gas to a patient and treating a respiratory disorder, the apparatus comprising:
   the flow generator according to claim 19;
   a pair of air delivery conduits, each air delivery conduit being connected to the respective outlet of the flow generator and being configured to convey the pressurized flow of breathable gas from the outlets; and
   the patient interface being adapted to be in communication with an entrance to a patient's airways, the patient interface being configured to be mounted on the patient's face and receive the pressurized flow of breathable gas from the pair of air delivery conduits.

27. The apparatus of claim 26, wherein the pair of air delivery conduits connect to the patient interface at opposite ends of the patient interface.

28. The apparatus of claim 26, wherein each of the pair of air delivery conduits is flexible.

* * * * *